US011559490B2

(12) United States Patent
Geissler et al.

(10) Patent No.: US 11,559,490 B2
(45) Date of Patent: Jan. 24, 2023

(54) PHARMACEUTICAL FORMULATION

(71) Applicant: Merck Patent GmbH, Darmstadt (DE)

(72) Inventors: Simon Geissler, Bad Homburg (DE); Martina Jeschke, Gross-Zimmern (DE); Patrizia Boniforte, Alsbach-Haehnlein (DE); Markus Weigandt, Mannheim (DE)

(73) Assignee: Merck Patent GmbH, Darmstadt (DE)

( * ) Notice: Subject to any disclaimer, the term of this patent is extended or adjusted under 35 U.S.C. 154(b) by 21 days.

(21) Appl. No.: 16/498,943

(22) PCT Filed: Mar. 28, 2018

(86) PCT No.: PCT/EP2018/057877
§ 371 (c)(1),
(2) Date: Sep. 27, 2019

(87) PCT Pub. No.: WO2018/178134
PCT Pub. Date: Oct. 4, 2018

(65) Prior Publication Data
US 2021/0085611 A1 Mar. 25, 2021

(30) Foreign Application Priority Data
Mar. 30, 2017 (EP) ..................................... 17163830

(51) Int. Cl.
| | | |
|---|---|---|
| A61K 9/20 | (2006.01) | |
| A61K 9/00 | (2006.01) | |
| A61K 9/10 | (2006.01) | |
| A61K 9/14 | (2006.01) | |
| A61K 9/16 | (2006.01) | |
| A61K 9/28 | (2006.01) | |
| A61K 9/48 | (2006.01) | |
| A61K 31/5377 | (2006.01) | |
| A61P 35/00 | (2006.01) | |
| C07D 413/14 | (2006.01) | |

(52) U.S. Cl.
CPC .......... *A61K 9/2027* (2013.01); *A61K 9/0053* (2013.01); *A61K 9/10* (2013.01); *A61K 9/141* (2013.01); *A61K 9/146* (2013.01); *A61K 9/16* (2013.01); *A61K 9/20* (2013.01); *A61K 9/2004* (2013.01); *A61K 9/205* (2013.01); *A61K 9/2009* (2013.01); *A61K 9/2022* (2013.01); *A61K 9/2054* (2013.01); *A61K 9/28* (2013.01); *A61K 9/4808* (2013.01); *A61K 9/4833* (2013.01); *A61K 9/4841* (2013.01); *A61K 31/5377* (2013.01); *A61P 35/00* (2018.01); *C07D 413/14* (2013.01)

(58) Field of Classification Search
None
See application file for complete search history.

(56) References Cited

U.S. PATENT DOCUMENTS

| | | |
|---|---|---|
| 9,732,094 B2 | 8/2017 | Fuchss et al. |
| 10,172,859 B2 | 1/2019 | Fuchss et al. |
| 10,383,874 B2 | 8/2019 | Fuchss et al. |
| 2014/0296267 A1* | 10/2014 | Fry ..................... A61K 9/0053 514/266.21 |
| 2016/0000720 A1 | 1/2016 | Bhavanasi et al. |
| 2016/0083401 A1 | 3/2016 | Fuchss et al. |
| 2016/0136283 A1 | 5/2016 | Warashina et al. |
| 2016/0346214 A1 | 12/2016 | Johnson et al. |
| 2017/0290836 A1 | 10/2017 | Fuchss et al. |
| 2019/0142833 A1 | 5/2019 | Fuchss et al. |

FOREIGN PATENT DOCUMENTS

| | | | |
|---|---|---|---|
| CN | 103998023 | 8/2014 | |
| JP | 2011509283 | 3/2011 | |
| JP | 2016098179 | 5/2016 | |
| JP | 2017505306 | 2/2017 | |
| WO | 2009/087410 | 7/2006 | |
| WO | WO-2009118167 A1 * | 10/2009 | ........... A61K 9/1635 |
| WO | 2012/164578 | 12/2012 | |
| WO | 2014/183850 | 11/2014 | |
| WO | 2015/119848 | 8/2015 | |
| WO | 2015/128298 | 9/2015 | |

OTHER PUBLICATIONS

Machine-assisted English translation of WO 2009/118167 A1. (Year: 2009).*
An internet article—Evonik "Eudragit functional polymers for oral solid dosage forms" (obtained from the website: https://healthcare.evonik.com/en/pharmaceuticals/oral-drug-delivery/oral-excipients/eudragit-portfolio). (Year unknown).*
International Search Report dated Jun. 21, 2018 in PCT/EP2018/057877.
Written Opinion dated Jun. 21, 2018 in PCT/EP2018/057877.
Smith et al., "The DNA-dependent protein kinase," Genes & Development 13:916-934, 1999.
Maškovskij M.D. Lekarstvenneye sredstva [Medicaments], 16th Ed.,Moscow: Novaâ volna, 2012, pp. 12-13.
Percev I.M., Farmacevtičeskie i medico-biologičeskie aspekty lekarstv, [Pharmaceutical and medico-biological aspects of medicaments], in 2 volumes, vol. 1, Kharkiv: UkrFA, 1999, pp. 253-255.
Russian Office Action dated Jul. 12, 2021 in Russian Application No. 2019133789, partial English translation only, 5 pages.
Sutâgin V. M. et al, Himiâ i fizica polimerov: Učebnoe posobie [The chemistry and physics of polymers: Textbook], Tomsk: Izdatel'stvo TPU, 2003, pp. 2 and 142. Flynn et al., "Pharmacokinetic Parameters", New Jersey Medical school, 2007, pp. 1-3.
Friesen et al., "Hydroxypropyl Methylcellulose Acetate Succinate-Based Spray-Dried Dispersions: An overview", Molecular Pharmaceutics, vol. 5, No. 6, 2008, pp. 1003-1019.

(Continued)

*Primary Examiner* — Sin J Lee
(74) *Attorney, Agent, or Firm* — Grüneberg and Myers, PLLC

(57) ABSTRACT

A pharmaceutical formulation has (S)-[2-chloro-4-fluoro-5-(7-morpholin-4-yl-quinazolin-4-yl)phenyl]-(6-methoxy-pyridazin-3-yl)methanol or pharmaceutically acceptable salt thereof.

27 Claims, 3 Drawing Sheets

(56) References Cited

OTHER PUBLICATIONS

Fule et al., "Artemether-Soluplus Hot-Melt Extrudate Solid Dispersion Systems for Solubility and Dissolution Rate Enhancement with Amorphous State Characteristics", Journal of Pharmaceutics, vol. 2013, Article ID 151432, 2013, 15 pages.
Japanese Office Action dated Jan. 6, 2022 in Japanese Application No. 2019-553415, with English Translation.
Maddineni et al., "Influence of Process and Formulation Parameters on Dissolution and Stability Characteristics of Kollidon® VA 34 Hot-Melt Extrudates", AAPS Pharm. Sci. Tech., vol. 16, No. 2, 2015, pp. 444-454.
Chinese Search Report dated Sep. 28, 2022, in Chinese Application No. 2018800221265, with English translation, 6 pages.
Pan Weisan, "Industrial Pharmacy", Medical Science and Technology Press, Beijing, China, Aug. 31, 2015, with English translation, 18 pages.

* cited by examiner

Figure 2: Powder X-ray diffraction pattern of crystalline "Form I"

PHARMACEUTICAL FORMULATION

CROSS-REFERENCE TO RELATED APPLICATIONS

This application is a National Stage entry under § 371 of International Application No. PCT/EP2018/057877, filed on Mar. 28, 2018, and which claims the benefit of European Application No. 17163830.7, filed on Mar. 30, 2017.

BACKGROUND OF THE INVENTION

The present invention relates to a pharmaceutical formulation of (S)-[2-chloro-4-fluoro-5-(7-morpholin-4-yl-quinazolin-4-yl)phenyl]-(6-methoxy-pyridazin-3-yl)methanol, as well as a method of making same, as well as medical uses thereof.

(S)-[2-chloro-4-fluoro-5-(7-morpholin-4-yl-quinazolin-4-yl)phenyl]-(6-methoxy-pyridazin-3-yl)methanol is disclosed as Example 136 in WO 2014/183850, as one member of a family of arylquinazolines which have been found to have valuable pharmacological properties. It is a potent and selective inhibitor of DNA-dependent protein kinase (DNA-PK) activity translating into potent inhibition of DNA-PK autophosphorylation in cancer cell lines, which has been demonstrated both by in vitro as well as in vivo data. It can therefore be used, in particular, for the sensitisation of cancer cells to anticancer agents and/or ionising radiation.

Human genetic material in the form of DNA is constantly subjected to attack by reactive oxygen species (ROS), which are formed principally as by-products of oxidative metabolism. ROSS are capable of causing DNA damage in the form of single-strand breaks. Double-strand breaks (DSBs) can arise if prior single-strand breaks occur in close proximity. In addition, single- and double-strand breaks may be caused if the DNA replication fork encounters damaged base patterns. Furthermore, exogenous influences, such as ionising radiation (for example gamma or particle radiation), and certain anticancer medicaments (for example bleomycin) are capable of causing DNA double-strand breaks. DSBs may furthermore occur as intermediates of somatic recombination, a process which is important for the formation of a functional immune system of all vertebrates.

If DNA double-strand breaks are not repaired or are repaired incorrectly, mutations and/or chromosome aberrations may occur, which may consequently result in cell death. In order to counter the severe dangers resulting from DNA double-strand breaks, eukaryotic cells have developed a number of mechanisms to repair them. Higher eukaryotes use predominantly so-called non-homologous end-joining, in which the DNA-dependent protein kinase (DNA-PK) adopts the key role. DNA-dependent protein kinase (DNA-PK) is a serine/threonine protein kinase which is activated in conjunction with DNA. Biochemical investigations have shown that DNA-PK is activated most effectively by the occurrence of DNA-DSBs. Cell lines whose DNA-PK components have mutated and are non-functional have proven to be radiation-sensitive (Smith and Jackson, 1999). DSBs are considered the most lethal type of DNA damage if left unrepaired.

(S)-[2-chloro-4-fluoro-5-(7-morpholin-4-yl-quinazolin-4-yl)phenyl]-(6-methoxy-pyridazin-3-yl)methanol has poor solubility in water and simulated gastric fluids. Also, in an amorphous form, the compound is voluminous and electrostatically charged and thus does not readily lend itself to further processing into a solid formulation. In addition, the manufacturing of a solid formulation of enantiomeric pharmaceutically active ingredients always bears the risk of undesirable conversion of the eutomer into the distomer.

It was therefore an object of the present invention to provide a pharmaceutical dosage form of (S)-[2-Chloro-4-fluoro-5-(7-morpholin-4-yl-quinazolin-4-yl)phenyl]-(6-methoxy-pyridazin-3-yl)methanol that would provide sufficient bioavailability and enantiomeric stability and a suitable process for its manufacture.

SUMMARY OF THE INVENTION

The present invention is directed to a composite comprising a solid dispersion of (S)-[2-chloro-4-fluoro-5-(7-morpholin-4-yl-quinazolin-4-yl)phenyl]-(6-methoxy-pyridazin-3-yl)methanol, or a pharmaceutically acceptable salt thereof, in a polymeric matrix.

(S)-[2-chloro-4-fluoro-5-(7-morpholin-4-yl-quinazolin-4-yl)phenyl]-(6-methoxy-pyridazin-3-yl)methanol is illustrated below:

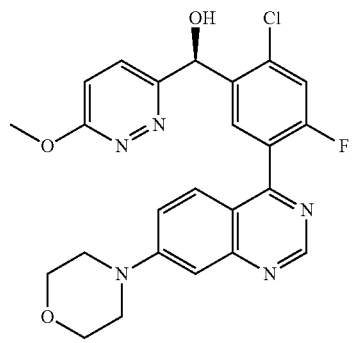 [SMILES: COc1ccc([C@@H](O)c2cc(-c3ncnc4cc(N5CCOCC5)ccc34)c(F)cc2Cl)nn1]

While reference is made herein throughout to the (S)-enantiomer of the compound, it is to be understood that the term (S)-[2-chloro-4-fluoro-5-(7-morpholin-4-yl-quinazolin-4-yl)phenyl]-(6-methoxy-pyridazin-3-yl)methanol in the present context shall be regarded as allowing a certain percentage of distomer impurity, preferably encompassing at most 10 wt. %, more preferably at most 5 wt. %, even more preferably at most 2 wt. %, and most preferably at most 1 wt. % or less of distomer impurity. Any amount or weight or weight percentage of the (S)-enantiomer, such as in the dispersion or pharmaceutical formulation given herein, thus includes both (S)-enantiomer and any unavoidable impurity of the (R)-enantiomer. (S)-[2-chloro-4-fluoro-5-(7-morpholin-4-yl-quinazolin-4-yl)-phenyl]-(6-methoxy-pyridazin-3-yl)methanol, in any form, may simply be referred to as the "drug substance" in the following.

The degree of enantiomeric impurity can be assessed using quantitative chiral HPLC, for instance as described in EXAMPLE 11.

The present invention further pertains to a pharmaceutical composition comprising said composite, methods of preparing the composite and methods of preparing the pharmaceutical composition, as well as the use of the composite respectively pharmaceutical composition in the treatment of cancer, either alone or in combination with radiotherapy and/or chemotherapy.

As set out above, in a first aspect, the present invention provides a composite comprising a solid dispersion of (S)-[2-chloro-4-fluoro-5-(7-morpholin-4-yl-quinazolin-4-yl)phenyl]-(6-methoxy-pyridazin-3-yl)methanol, or a pharmaceutically acceptable salt thereof, in a polymeric matrix. In some embodiments, the composite may comprise the solid dispersion as well as one or more pharmaceutically acceptable excipients, for instance selected from a filler (e.g. polysaccharide, disaccharide, polyalcohols), disintegrant (e.g. polyvinylpolypyrrolidon), non-ionic and ionic surfactants (e.g. poloxamer, magnesium stearate, sodium lauryl sulphate), plasticizers (e.g. polyalkylene glycol) and inorganic absorbers (e.g. silica).

A solid dispersion, as used herein, refers to a drug substance, which is dispersed or distributed in a dispersion medium, which is a polymeric matrix in accordance with the present invention. Based upon the possible combinations of drug substance and polymer physical states, the drug substance can be either crystalline or amorphous and the polymeric matrix can also be crystalline and amorphous, resulting in four possible combinations: crystalline drug substance—crystalline polymer (solid suspension); amorphous drug substance—amorphous polymer; crystalline drug—amorphous polymer; and amorphous drug—crystalline polymer. Exemplary embodiments herein relate to amorphous drug substance in polymeric matrix, Amorphous drug substance can be dispersed in the form of amorphous (micro)particles in an amorphous polymeric matrix, which is then referred to as an amorphous suspension, or it can be molecularly dispersed in a (crystalline or amorphous) polymer or polymeric matrix to form a solid solution. A "solid solution" in the sense of the invention, shall still encompass those embodiments wherein a small portion of the drug substance may have come out of solution or remain undissolved, provided that, for instance, at least about 80%, more preferably at least about 90% and most preferably at least about 95% or at least about 99% of the drug substance (by volume) shall be in the molecularly dispersed state. In such a solid solution, the individual physical properties of the drug substance are no longer recognizable.

In a preferred embodiment, the composite according to the present invention consists of the solid dispersion of (S)[2-chloro-4-fluoro-5-(7-morpholin-4-yl-quinazolin-4-yl)phenyl]-(6-methoxy-pyridazin-3-yl)methanol, or a pharmaceutically acceptable salt thereof, in the polymeric matrix. Of course, it may then simply be referred to as the solid dispersion.

Most preferably, the solid dispersion is a solid solution, i.e. most preferably, the drug substance is molecularly dispersed in the polymeric matrix.

As apparent from the exemplary embodiments described herein, the obtained solid dispersions are amorphous.

While (S)-[2-chloro-4-fluoro-5-(7-morpholin-4-yl-quinazolin-4-yl)phenyl]-(6-methoxy-pyridazin-3-yl)methanol may be present in any suitable salt form, it is most preferably present in its free form, rather than a salt form.

Pharmaceutically acceptable salts include those mentioned in the disclosure of WO 2014/183850, which is incorporated by reference herein in its entirety.

Any reference to amounts or weights or weight percentages of (S)-[2-chloro-4-fluoro-5-(7-morpholin-4-yl-quinazolin-4-yl)phenyl]-(6-methoxy-pyridazin-3-yl)methanol or pharmaceutically acceptable salts thereof, shall be taken to refer to the anhydrous free form of (S)-[2-chloro-4-fluoro-5-(7-morpholin-4-yl-quinazolin-4-yl)phenyl]-(6-methoxy-pyridazin-3-yl)methanol (including distomer, if applicable, as set our above), unless specified otherwise herein.

In order to form a solid dispersion, the polymer or polymers forming the polymeric matrix are generally polymers that are capable of embedding the drug substance, in particular when heated above the melting point, especially in a melt granulation or melt extrusion process or when dissolved in a solvent and atomized, such as in a spray-drying process. The polymer forming the polymeric matrix therefore preferably exhibits thermoplastic behaviour. Any polymer capable of thus embedding the drug substance, most preferably at a molecular level, and enhancing its dissolution may be used in the context of the present invention. Hydrophilic polymers are therefore preferred.

In a preferred embodiment, the polymeric matrix comprises or consists of a homopolymer or copolymer of polyvinylpyrrolidone. More preferably, the polymeric matrix comprises or consists of a copolymer of polyvinylpyrrolidone, and most preferably a copolymer of polyvinylpyrrolidone and polyvinylacetate. Most preferably, the solid dispersion consists of (S)-[2-chloro-4-fluoro-5-(7-morpholin-4-yl-quinazolin-4-yl)phenyl]-(6-methoxy-pyridazin-3-yl)methanol, most preferably in its free form, in a polymeric matrix of a copolymer of polyvinylpyrrolidone and polyvinylacetate. As will be shown in relation to exemplary embodiments, this embodiment is particularly beneficial in that it can be prepared with only minimal conversion of (S)-[2-chloro-4-fluoro-5-(7-morpholin-4-yl-quinazolin-4-yl)phenyl]-(6-methoxy-pyridazin-3-yl)methanol to the distomer ((R)-enantiomer). Even after extended storage, the eutomer:distomer ratio is highly satisfactory. Considering that, based upon current estimates of clinically effective doses, the amount to be taken by the patient and thus to be incorporated into the pharmaceutical dosage form is substantial, this is a highly important factor to be taken into account. Preferably, the solid dispersion is obtainable by holt melt extrusion.

The copolymer of polyvinylpyrrolidone and polyvinylacetate may also be referred to/encompass vinylpyrrolidone-vinyl acetate copolymer, copovidone (USP), copolyvidone (JPE), PVP-VAc-Copolymer, or: acetic acid ethenyl ester, polymer with 1-ethenyl-2-pyrrolidinone (IUPAC). Any of these terms may be used in the following, with copovidone being given preference for the sake of simplicity. The CAS number of the copolymer is 25086-89-9. An example of a suitable commercially available copovidone is Kollidon® VA 64 (BASF). According to the manufacturer's information, the Kollidon® VA 64 grades are manufactured by free radical polymerization of 6 parts N-vinylpyrrolidone and 4 parts vinylacetate in 2-propanol, in accordance with the cGMP regulations, which yields a water-soluble polymer with a chain structure. It is further reported (BASF) to have a K-value in the range of 25.2-30.8 (nominally 28), the K-value being determined in accordance with the European pharmacopoeia, i.e. calculated from the relative viscosity (kinematic) of a 1% solution in water at 25° C. The glass transition temperature of Kollidon® VA 64 depends on the moisture content and is at 103° C. for dry Kollidon® VA 64.

In an alternative preferred embodiment, the polymeric matrix comprises or consists of a polyvinyl caprolactam—polyvinyl acetate—polyethyleneglycol graft copolymer. A suitable commercially available polymer is designated Soluplus® (BASF). According to the manufacturer's information, the average molecular weight of that product as measured by gel permeation chromatography is typically in the range of 90.000 to 140:000 g/mol, CAS number of the copolymer is 402932-23-4.

In an alternative embodiment, the polymeric matrix comprises or consists of hypromellose acetate succinate. The polymer may also be referred to as hydroxypropyl methylcellulose acetate succinate, or: Cellulose, 2-hydroxypropyl methyl ether, acetate, hydrogen butanedioate (IUPAC), or be abbreviated as HPMCAS. The CAS registry number is 71138-97-1. An example of a commercially available suitable example of the hypromellose acetate succinate is Aqoat® (Shin-Etsu). Particularly preferred herein for melt processing, in particular hot melt extrusion, is the micronized variant, e.g. Aqoat® AS-LF, which, according to the manufacturer's information, comprises 8% acetyl groups and 15% succinyl groups, has a weight-average molecular weight of 18,000 (measured with SEC-MALS) and a mean particle size of 5 μm. Preferred herein for other manufacturing processes, in particular spray-drying, is another micronized variant, e.g. Aqoat® AS-HF, which, according to the manufacturer's information, comprises 12% acetyl groups and 6% succinyl groups and has a mean particle size of 5 μm.

As will be apparent, in particular from the solid dispersions obtained by spray-drying, embodiments wherein the polymeric matrix comprises or consists of hypromellose acetate succinate are equally very advantageous and therefore preferred herein.

In a further alternative embodiment, the polymeric matrix comprises or consists of basic butylated methacrylate copolymer (USP: amino methacrylate polymer). A suitable example of such a polymer is Eudragit®, for instance (CAS number 24938-16-7), such as Eudragit® E100 or E PO, According to the manufacturer's specification, Eudragit® E100 is cationic polymer based on dimethylaminoethyl methacrylate, butyl methacrylate and methyl methacrylate with a ratio of 2:1:1. The monomers are randomly distributed along the copolymer chain. Based on the SEC method, the weight average molecular mass of Eudragit® E100 or E PO is approximately 47,000 g/mol. Eudragit® E PO has a particle size determined by laser light diffraction according to Ph. Eur. 2.9.31/light diffraction measurement USP <429> of Dv50<50 μm.

In a further exemplary embodiment, the polymeric matrix may comprise or consist of HPMCP. HPMCP is short for hypromellose phthalate, which is a monophthalic acid ester of hydroxypropylmethylcellulose. It contains methoxy, hydroxypropoxy and phthalyl groups. HPMCP has CAS registry number 9050-31-1. Suitable examples are the HPMCP grades available from Shin-Etsu Further polymers known in the art, such as macrogols, PEO homopolymers or copolymers, polyacrylate homopolymers or copolymers, cellulose ethers and polysaccharides are further conceivable polymers that may form the polymeric matrix.

The polymeric matrix in the solid dispersion according to the present invention may comprise more than one polymer forming the matrix. In preferred embodiments, however, the polymeric matrix comprises only one polymer. In addition, the polymeric matrix may or may not comprise one or more additives, such as one or more plasticizers. Exemplary plasticizers known in the art include polyalkylene glycol, polyoxyethylene-polyoxypropylene block copolymer (e.g. Kolliphor® P188, P338, P407), polysorbate (e.g. Tween®), tributyl citrate, triethyl citrate, acetyltriethyl citrate, acetyltributyl citrate, citric acid monohydrate, triacetin, dioctyl phthalate, diethyl phthalate, dibutyl sebacate, castor oil and derivatives thereof, e.g. PEG-40 hydrogenated castor oil.

In some exemplary embodiments, additional pharmaceutically acceptable excipients are already provided in admixture with the polymer for forming the polymeric matrix. However, "polymer" as used herein is not to be understood as a blend of a polymer with additives, it shall refer to a polymer as such.

In preferred embodiments, the solid dispersion, more preferably solid solution, consists only of the drug substance in the polymeric matrix, which is formed by one polymer without any further additives (2-component-system).

The solid dispersion according to the present invention is obtainable, for instance, by hot melt extrusion or melt granulation Hot melt extrusion is particularly preferred as it has been found to provide the most beneficial properties of the dispersion, respectively composite. Thus, preferably, the solid dispersion is a hot melt extrudate.

In alternative exemplary embodiments, a solid dispersion according to the present invention is obtainable by solvent-based processes, most preferably and advantageously spray drying.

Co-precipitation, lyophilisation or solvent casting are further processes that are generally available to produce solid dispersions according to the present invention.

Preferably, in the composite according to the invention, in particular in the solid dispersion itself, the concentration of (S)-[2-chloro-4-fluoro-5-(7-morpholin-4-yl-quinazolin-4-yl)phenyl]-(6-methoxy-pyridazin-3-yl)methanol, which may be present in free form or in the form of a pharmaceutically acceptable salt, in the polymeric matrix is in a range of between 4 and 60 weight percent, such as between 4 and 50 weight percent, preferably between 10 to 40 weight percent, for instance between 15 to 30 wt. %, or 17.5 to 25 wt. %, based on the total weight of solid dispersion.

For the sake of clarity, it shall be reiterated that the weight percentage refers to the anhydrous free form, irrespective of whether the drug substance is contained in free form or in the form of one of its pharmaceutically acceptable salt.

Expressed differently, the solid dispersion may, for instance, comprise at least 4 wt. % (S)-[2-chloro-4-fluoro-5-(7-morpholin-4-yl-quinazolin-4-yl)phenyl]-(6-methoxy-pyridazin-3-yl)methanol, at least 10 wt. % (S)-[2-chloro-4-fluoro-5-(7-morpholin-4-yl-quinazolin-4-yl)phenyl]-(6-methoxy-pyridazin-3-yl)methanol, at least 15 wt. % (S)-[2-chloro-4-fluoro-5-(7-morpholin-4-yl-quinazolin-4-yl)phenyl]-(6-methoxy-pyridazin-3-yl)methanol or at least 17.5 wt. % (S)-[2-chloro-4-fluoro-5-(7-morpholin-4-yl-quinazolin-4-yl)phenyl]-(6-methoxy-pyridazin-3-yl)methanol, Again, as above, the drug substance may be present in free form or salt form, with the weight percentages being calculated presuming the anhydrous free form.

In exemplary embodiments, the solid dispersion consists of 15 to 35 wt. % (S)-[2-chloro-4-fluoro-5-(7-morpholin-4-yl-quinazolin-4-yl)phenyl]-(6-methoxy-pyridazin-3-yl) methanol and 65 to 85 wt. % polymeric matrix, preferably made up by only one polymer without any further additives. In other exemplary embodiments, the solid dispersion consists of 15 to 30 wt. % (S)-[2-chloro-4-fluoro-5-(7-morpholin-4-yl-quinazolin-4-yl)phenyl]-(6-methoxy-pyridazin-3-yl)-methanol and 70 to 85 wt. % polymeric matrix, preferably made up by only one polymer without any further additives.

In further exemplary embodiments, the solid dispersion consists of 15 to 25 wt. % (S)-[2-chloro-4-fluoro-5-(7-morpholin-4-yl-quinazolin-4-yl)phenyl]-(6-methoxy-pyridazin-3-yl)methanol and 75 to 85 wt. % polymeric matrix, preferably made up by only one polymer without any further additives.

In one exemplary embodiment, the solid dispersion consists of 20 wt. % (S)-[2-chloro-4-fluoro-5-(7-morpholin-4-yl-quinazolin-4-yl)phenyl]-(6-methoxy-pyridazin-3-yl) methanol and 80 wt. % polymeric matrix, preferably made up by only one polymer without any further additives.

In another exemplary embodiment, the solid dispersion consists of 25 wt. % (S)-[2-chloro-4-fluoro-5-(7-morpholin-4-yl-quinazolin-4-yl)phenyl]-(6-methoxy-pyridazin-3-yl) methanol and 75 wt. % polymeric matrix, preferably made up by only one polymer without any further additives.

In another exemplary embodiment, the solid dispersion consists of 30 wt. % (S)-[2-chloro-4-fluoro-5-(7-morpholin-4-yl-quinazolin-4-yl)phenyl]-(6-methoxy-pyridazin-3-yl) methanol and 70 wt. % polymeric matrix, preferably made up by only one polymer without any further additives. All in all, and as will be apparent from the examples, the solid dispersions according to the present invention provide good bioavailability. While solid dispersions are known to be potentially beneficial to enhance bioavailability of poorly soluble active ingredients, the science underlying this technology is not yet fully understood and small scale screening methods do not necessarily provide good correlation to larger scale production methods. Still, the inventors of the present invention have succeeded at providing solid dispersions, in particular amorphous solid dispersions of the drug substance that provide better bioavailability than any of the hitherto known salt and polymorphic forms.

Copovidone has proven particularly useful as/in a polymeric matrix in the solid dispersions, as it can be made either by spray-drying or hot melt extrusion, with the resulting amorphous solid dispersions being characterized by good stability, very low amounts of distomer and degradation products being generated and excellent long term stability. Molecular dispersion of the drug substance in the polymeric matrix provides for those advantages. These advantages are all the more surprising since small scale screening efforts did not provide any indication of these results, but would rather have eliminated this polymer from further consideration.

A further preferred polymer, in particular for solid dispersions prepared by spray-drying is hypromellose acetate succinate.

The composite according to the present invention, in particular when obtained by melt processing such as hot melt extrusion, may have a particle size characterized by a $d_{50}$ value of 1000 μm or less, preferably 500 μm or less, more preferably 400 μm or less, 300 μm or less, for instance between 200 μm and 300 μm. Generally, a smaller particle size is associated with a higher surface area, which may be beneficial in terms of dissolution, but typically requires a mechanical decrease of the original particles, which is often associated with the generation of heat and may therefore have a negative impact on other physical parameters of the particles, such as density, but also the dispersion of drug substance within the matrix, and even impurity levels. The d50 values referred to herein are measured by laser diffraction on a Malvern Mastersizer 2000 (dry method; micro volume tray; sample amount of 200 mg; dispersive air pressure of 0.1 bar; feed rate of 50%; measuring time of 4 s; obscuration of 1-5%; use of 66 dispersive steel balls a 2 mm; measurements evaluated with the MIE theory). The d50 value referred to herein is the size in micrometres that splits the distribution with half above and half below this diameter. The d50 is the median for a volume distribution and is often also designated Dv50 (or Dv0.5).

In those embodiments wherein the composite, more particular dispersion is obtained by spray drying, the particle size is usually in a range that is characterized by a $d_{50}$ value from 1 μm to 300 μm, preferably from 20 μm to 200 μm and more preferably from 30 to 100 μm. Accordingly, one embodiment of the invention is also directed to the composite, wherein the composite has a mean particle size that is characterized by a d50 value of less than 200 μm, for instance less than 100 μm, for instance in the range from 1 μm to 300 μm, preferably from 20 μm to 200 μm and more preferably from 30 μm to 100 μm.

If the particle size is smaller than desired, for instance because small particle size may not be ideal in terms of flowability or density for subsequent processing steps into the final composition, particle size may be increased using suitable techniques such as granulation or roller compaction. Such techniques are used to prepare granulates that may have a particle size characterized by a d50 value of 1000 μm or less, preferably 500 μm or less, more preferably 400 μm or less, 300 μm or less, for instance between 200 μm and 300 μm.

Accordingly, the present invention is also directed to a composite in the form of a granulate, wherein such granulate has a particle size that is characterized by a d50 value of 1000 μm or less, preferably 500 μm or less, more preferably 400 μm or less, 300 μm or less, for instance between 200 μm and 300 μm.

The present invention also provides a pharmaceutical composition comprising the composite according to the invention. Most preferably, the pharmaceutical composition is for oral administration.

More preferably still, the pharmaceutical composition is an immediate release composition. In exemplary embodiments, the pharmaceutical composition, most preferably tablet, is characterized by a disintegration time of 30 minutes or less, such as 20 minutes or less, preferably 15 minutes or less, and more preferably 10 minutes or less. The disintegration time referred to above is measured in 0.01 N HCl at 37° C. in a disintegration apparatus according to USP-NF <701> (USP39-NF34 Page 537; *Pharmacopeial Forum*: Volume No. 34(1) Page 155) Disintegration: The apparatus consists of a basket-rack assembly, a 1000-mL, low-form beaker for the immersion fluid, a thermostatic arrangement for heating, and a device for raising and lowering the basket in the immersion fluid. The basket-rack assembly moves vertically along its axis and consists of six open-ended transparent tubes; the tubes are held in a vertical position by two plates.

Attached to the under surface of the lower plate is a woven stainless steel wire cloth. Each tube is provided with a cylindrical disk. The disk is made of a suitable transparent plastic material, Place 1 dosage unit in each of the six tubes of the basket and add a disk. Operate the apparatus, using the specified medium as the immersion fluid, maintained at 37° C.±2° C. At the end of the time limit or at preset intervals, lift the basket from the fluid, and observe whether the tablets have disintegrated completely.

In one embodiment, the pharmaceutical composition according to the present invention is a capsule containing a filling comprising the composite and optionally at least one pharmaceutically acceptable excipient. The capsule itself may be any pharmaceutically acceptable capsule, such as a hard gelatin capsule, but should preferably be easily dissolvable.

In an exemplary embodiment, the pharmaceutical composition is a capsule, which contains a filling consisting of 40 to 100 wt. %, for instance at least 50 wt. %, more preferably at least 70, 80, 90, 95 or 99 wt. % of the composite according to the present invention; and 0 to 60 wt. %, i.e. the remainder (difference to 100 wt. %) of the filling, of at least one pharmaceutically acceptable excipient, preferably selected from a filler, a disintegrant, a lubricant, a pore builder and an inorganic alkaline metal salt, based upon the total weight of the filling. In other words, the capsule does not count in the calculation of the weight percentages as given herein.

As will be shown by way of examples, capsule formulations may comprise, for instance, 100, 99.5, 99, 90, 80, 75, 70, 60 or 50 wt. % of the composite respectively solid dispersion in those embodiments where the composite consists of solid dispersion, or any range enclosed by any combination of those values: 50 to 100 wt. %, 50 to 99.5 wt. %, 50 to 99 wt. %, 50 to 90 wt. %, 50 to 80 wt. %, 50 to 75 wt. %, 50 to 70 wt. %, 50 to 60 wt. %; 60 to 100 wt. %, 60 to 99.5 wt. %, 60 to 99 wt. %, 60 to 90 wt. %, 60 to 80 wt. %, 60 to 75 wt. %, 60 to 70 wt. %; 70 to 100 wt. %, 70 to 99.5 wt. %, 70 to 99 wt. %, 70 to 90 wt. %, 70 to 80 wt. %; 75 to 100 wt. %, 75 to 99.5 wt. %, 75 to 99 wt. %, 75 to 90 wt. %, 75 to 80 wt. %; 80 to 100 wt. %, 80 to 99.5 wt. %, 80 to 99 wt. %, 80 to 90 wt. %; 90 to 100 wt. %, 90 to 99.5 wt. %, or 90 to 99 wt. %, The remainder of the filling (difference to 100 wt. %) is made up by at least one pharmaceutically acceptable excipient, as set out above.

In an exemplary embodiment, the pharmaceutical composition is a capsule containing a filling comprising:
  50 to 100 wt. % of the composite according to the invention;
  2.5 to 75 wt. % of disintegrant;
  0 to 60 wt. % of a filler;
  0 to 5 wt. % of a lubricant;
  0 to 30 wt. % of a pore builder;
  0 to 20 wt. % of an inorganic alkaline metal salt; and
  a total of 0 to 20 wt. % of one or more additional pharmaceutically acceptable excipients, based upon the total weight of the tablet. Total weight, of course, means 100 wt. %.

The weight percentage of the disintegrant in the above exemplary embodiment may be in a range of 5 to 60 wt. %, for instance, or a range of 7.5 to 55 wt. %, for instance, or a range of 7.5 to 25 wt. %, for instance.

The weight range of the lubricant in the above exemplary embodiment may be in a range of 0.25 wt. % to 5 wt. %, or 0.5 wt. % to 4 wt. %, or 0.5 wt. % to 2.5 wt. %, for instance.

Pore builder, if present in the above exemplary embodiment, may be comprised in an amount of 2.5 to 50 wt. %, or 5 to 25 wt. %, or 7.5 to 20 wt. %, for instance.

Filler, if present, may be present in the above exemplary embodiment, for instance, in a range of up to 60 wt. %, such as 5 to 60 wt. %, or a range of 7.5 to 55 wt. %, or up to 50 wt. %, or in a range of 10 to 50 wt. %, for instance. Embodiments of capsules without filler have also been found to be feasible.

Inorganic alkaline metal salt is preferably present in the above exemplary embodiment, and may be comprised in an amount of 2.5 to 20 wt. %, or 5 to 17.5 wt. %, for instance, or at least 7.5 wt. %, for instance around 10 or 15 wt. %.

Examples of suitable pharmaceutically acceptable excipients of the above categories include:

Fillers generally serve to create desired bulk, flow properties, and compression characteristics in the preparation of tablets and capsule fillings. Suitable fillers include: cellulose, including modified cellulose, such as microcrystalline cellulose, cellulose ethers, such as HPMC (hydroxypropylmethylcellulose), lactose, and dextrose, to name but a few. Microcrystalline cellulose is particularly preferred.

Disintegrants serve to disintegrate tablets or granules etc. and thus enhance dissolution of the solid dosage form upon contact with the liquid dissolution medium. Suitable disintegrants include crospovidone (cross linked polyvinyl N-pyrrolidone), carboxymethylcellulose and salts and derivatives thereof, such as crosslinked derivatives, for instance croscarmellose sodium (cross-linked polymer of carboxymethylcellulose sodium,) sodium carboxymethyl glycolate, sodium starch glycolate, carrageenan, agar, and pectin. Crospovidone and croscarmellose sodium are particularly preferred.

Lubricants serve to prevent sticking of ingredients to one another of the capsule filling or tablet compressing machines. Even though not strictly identical with glidants, which serve to reduce interparticular friction and thus enhance flowability of a particle mixture in the manufacture of tablets or capsules, glidants and lubricants are collectively referred to as lubricants herein. A lubricant that may be used in the context of the present invention is selected from one or more of the following: magnesium stearate, stearic acid, talc, stearin, silica, such as hydrophilic fumed silica or colloidal silica, magnesium trisilicate, starch, magnesium carbonate, magnesium oxide, calcium phosphate ($Ca_3(PO_4)_2$), calcium stearate, and aluminum stearate. Magnesium stearate is particularly preferred.

Among pore builders or pore-formers, mannitol, sucrose and esters thereof, trehalose or cyclodextrins may be mentioned as suitable for use in the present invention, with mannitol being particularly preferred.

Inorganic alkaline metal salts, i.e. salts made up of ions of alkaline metals and inorganic acid anions, have relatively recently been found useful for enhancing dissolution and include sodium chloride, sodium sulphate, sodium carbonate, sodium bicarbonate, sodium phosphate, sodium dihydrogen phosphate, potassium chloride, potassium carbonate, and potassium bicarbonate. Sodium chloride is particularly preferred.

In a more preferred embodiment, the pharmaceutical composition is selected from a tablet and a granulate, and therefore typically comprises at least one pharmaceutically acceptable excipient. The at least one pharmaceutically acceptable excipient is preferably selected from a filler, a disintegrant, a lubricant, a pore builder, an inorganic alkaline metal salt or a combination thereof.

In an exemplary embodiment, the pharmaceutical composition is a tablet comprising:
  25 to 95 wt. % of the composite according to the invention
  15 to 72.5 wt. % of a filler;
  2.5 to 40 wt. % of disintegrant;
  0 to 5 wt. % of a lubricant;
  0 to 20 wt. % of an inorganic alkaline metal salt; and
  a total of 0 to 20 wt. % of one or more additional pharmaceutically acceptable excipients, based upon the total weight of the tablet.

The one or more additional pharmaceutically acceptable excipients may include one or more selected from pore builders, preservatives, antioxidants, sweeteners, flavours, dyes, surfactants, and wicking agents.

Many excipients may exert more than one function, depending on the other components of the pharmaceutical dosage form. For the sake of clarity, in particular in calculating weight percentages, each pharmaceutically acceptable excipient used in a pharmaceutical composition according to the present invention is preferably associated with one functionality only, i.e. is either regarded as a disintegrant or a lubricant.

In another exemplary embodiment, the pharmaceutical composition is a tablet comprising:
  40 to 60 wt. % of the composite according to the invention;
  25 to 55 wt. % of a filler;
  5 to 30 wt. % of disintegrant;
  0 to 5 wt. % of a lubricant;
  0 to 15 wt. % of an inorganic alkaline metal salt; and
  a total of 0 to 10 wt. % of one or more additional pharmaceutically acceptable excipients, based upon the total weight of the tablet.

In a further exemplary embodiment, the pharmaceutical composition is a tablet comprising:
- 35 to 55 wt. % of the composite according to the invention;
- 30 to 55 wt. % of a filler;
- 5 to 20 wt. % of disintegrant;
- 0.25 to 2.5 wt. % of a lubricant;
- 2.5 to 15 wt. % of an inorganic alkaline metal salt; and
- a total of 0 to 10 wt. % of one or more additional pharmaceutically acceptable excipients, based upon the total weight of the tablet.

Preferably, in those embodiments, the filler is microcrystalline cellulose and/or the disintegrant is selected from crospovidone, carboxymethylcellulose and salts and derivatives thereof, such as croscarmellose sodium, and/or the inorganic alkaline metal salt is an inorganic sodium salt, such as sodium chloride.

Preferably, the total of one or more additional pharmaceutically acceptable excipients is 0 to 10 wt. %, 0 to 7.5 wt. %, 0 to 5 wt. %, 0 to 2.5 wt. % or 0 to 1 wt. %, for instance 0 wt. %.

Of course, the tablet may be coated, to improve taste and/or appearance and/or to protect the tablet from external influences such as moisture. Any coating shall not count towards the total of 100 wt. % of pharmaceutically active ingredients and drug substance making up the tablets, as listed above. For film-coating, macromolecular substances, such as modified celluloses, including hydroxypropylmethylcellulose (HPMC), polymethacrylates, and zein may be used, for example. The thickness of the coating is preferably less than 100 μm.

In alternative embodiments, the pharmaceutical composition may take any other form suitable for incorporating the solid dispersion respectively composite according to the present invention. Lozenges, caplets, pastilles may be mentioned.

The present invention also provides a first method for preparing the composite, which comprises or consists of the solid dispersion, which is preferably a solid solution, wherein the method comprises hot melt-extrusion or melt granulation-. Hot-melt extrusion has been found to provide the best physical properties for the solid dispersion and is therefore particularly preferred herein.

In an exemplary embodiment, the method comprises:
mixing and melting (S)-[2-chloro-4-fluoro-5-(7-morpholin-4-yl-quinazolin-4-yl)-phenyl]-(6-methoxy-pyridazin-3-yl)methanol, or a pharmaceutically acceptable salt thereof, and the polymer of the polymeric matrix to be formed, and optionally at least one pharmaceutically acceptable excipient,
hot melt extruding or melt granulating the mixture to form the composite,
and optionally milling the formed composite.

Of course, mixing and melting may comprise mixing the polymer and the drug substance, followed by a melting step, which necessarily involves further mixing, or a single step of mixing and melting. Mixing and melting is, as known in the art, to be understood in the sense of mixing (S)-[2-chloro-4-fluoro-5-(7-morpholin-4-yl-quinazolin-4-yl)phenyl]-(6-methoxy-pyridazin-3-yl)methanol, or a pharmaceutically acceptable salt thereof, and the polymer of the polymeric matrix to be formed, and optionally at least one pharmaceutically acceptable excipient, while melting the polymer. (S)-[2-chloro-4-fluoro-5-(7-morpholin-4-yl-quinazolin-4-yl)phenyl]-(6-methoxy-pyridazin-3-yl)methanol, or pharmaceutically acceptable salt thereof, is thus dissolved or dispersed in the melt, rather than melting itself.

Suitable hot melt extruders are known in the art. Suitable extruders include small scale extruders such as HAAKE MiniLab II (Thermo Fisher Scientific) or larger scale co-rotating twin screw extruders, such as PharmaLab 16 (Thermo Fisher Scientific, screw diameter 16 mm), or ZSE 18 HP-PH (Leistritz, screw diameter 18 mm), to name but a few examples.

Suitable adjustment of the process parameters, such as melt temperature, melt pressure, torque, and extrusion input parameters, such as temperature profile, throughput, screw design and screw speed, can be readily accomplished by routine experimentation based upon the common general knowledge of the person skilled in the art.

Suitable mills for the optional milling step are also known in the art. Suitably, a hammer mill (such as FitzMill L1A by Fitzpatrick) may be used.

In an alternative embodiment, the present invention also provides a second method for preparing the composite, which composite comprises or consists of the solid dispersion, which is preferably a solid solution, wherein the method comprises
a) Dissolving the drug substance and the polymer of which the polymeric matrix is to be formed, and optionally one or more pharmaceutically acceptable excipients, in a solvent to form a solution,
b) Spray-drying the solution to form the composite,
c) Optionally drying the composite, preferably under reduced pressure.

For the drug substance and polymers used according to the present invention, suitable solvents include: dichloromethane, methanol and most preferably mixtures thereof. Other suitable solvent systems will present themselves to the skilled person taking into account solubility of the drug substance, an indication of which can be taken from EXAMPLE 1, and the solubility of the polymer forming the polymeric matrix, as per the manufacturers information.

Of course, dissolving may comprise dissolving the drug substance and polymer in the solvent, which may be done successively by firstly dissolving the drug substance to form a solution of the drug substance and secondly adding and dissolving the polymer to the solution of drug substance or vice versa, i.e. by firstly dissolving the polymer in the solvent and then adding the polymer. Alternatively, solutions of the drug substance and the polymer can be prepared separately and then both solutions are unified to one solution.

Suitable spray-drying techniques which can be used for preparation of the particles are well known and described, for example, by K. Masters in "Spray-drying Handbook", John Wiley & Sons, New York, 1984. In an exemplary embodiment, atomization of the solution is performed by using a nozzle. Examples of suitable spray-driers include lab scale spray-dryers, such as the Mini Spray Dryer 290 (Buchi) or 4M8-TriX (ProCepT); or a MOBILE MINOR™, a Pharma Spray Dryer PharmaSD® from GEA Niro.

The spray-drying conditions have a major impact on product properties, solvent content, particle size, morphology and the extent of degradation of drug substance and polymer. Temperature is the most important process parameter, since the exposure of the drug substance and polymer to high temperature could cause degradation. For the spray-dryer, two temperatures have to be controlled: inlet temperature and outlet temperature. The former is an independent process parameter and it can be set by the operator, the latter is dependent e.g. on the liquid feed rate, the atomizing gas volumetric flow rate (if used), the drying gas volumetric flow rate, and the inlet temperature chosen. The process parameters can be readily accomplished by routine experimentation based upon the common general knowledge of the person skilled in the art.

Suitable drying techniques which can be used for the optional drying step include ordinary techniques known in the art, such as, for example drum, belt and tray drying. Such techniques can be performed under air or nitrogen atmosphere at normal or reduced pressure, e.g. under vacuum. Drying under reduced pressure is preferred.

Suitable analytical methods for assessing amorphous nature, integrity of the drug substance and eutomer-distomer ratio are described in EXAMPLE 11.

Preferably, as a starting material for the hot melt extrusion or melt granulation process, or spray drying or co-precipitation, a crystalline form of the drug substance is used. Most preferably, a crystalline form of the free drug substance is used, which shall be referred to as Form I in the following, and which is characterized by an X-ray powder diffraction pattern having at least two peaks at degrees two theta (°2θ) selected from 4.1, 5.2, 6.1, 8.3, 8.5, 10.1, 10.9, 12.7, 13.0, 13.8, 14.7, 15.0, 18.6, 19.2, 20.0, 20.5, 20.8, 21.3, 22.0, 22.4, 22.8, 23.4, 24.4, each ±0.2 degrees two theta, wherein at least one of the at least two peaks is selected from 4.1, 5.2, 8.3, 8.5, 10.1, 10.9, 12.7, 13.0 and 21.3 degrees two theta (°2θ), each peak ±0.2 degrees two theta. This crystalline form is obtainable by slow crystallization from a heated solvent or solvent mixture, such as methanol, ethanol, 1-propanol, acetone, methyl ethyl ketone, methyl isobutyl ketone, ethyl acetate, tetrahydrofurane, acetonitrile, and mixtures of two or more of these. An example of a suitable method of preparing said crystalline form is described in EXAMPLE 1.

Crystalline form I crystallises in the orthorhombic space group $P2_12_12_1$ with the lattice parameters a=4.8 Å, b=27.5 Å, c=33.3 Å and α=β=γ=90°. The form may be further characterized in that there are 8 formula units per unit cell and the unit cell volume is 4436 Å$^3$. The crystalline form may further be described by a calculated density of 1.44 g/cm$^3$. These data were generated based upon single crystal X-ray structure data using a Rigaku SuperNova diffractometer, equipped with CCD detector using Cu-Kα radiation at 200 K. Form I shows no thermal events prior to melting/decomposition above 200° C.

Thus, the present invention also pertains to the use of Form I in a method for manufacturing a composite according the present invention.

The present invention further provides a method for preparing a pharmaceutical composition comprising the composite according to the invention, which method comprises a method to form the composite as set out above;

mixing the composite and one or more pharmaceutically acceptable excipients;

optionally granulating the mixture of the composite and the one or more pharmaceutically acceptable excipients, and either filling the (optionally granulated) mixture into capsules or tableting the mixture.

It is to be understood that mixing the composite and excipients and granulating the mixture may be part of the same step, i.e. occur simultaneously.

Tableting respectively compressing into tablets can be performed with commonly used eccentric presses or rotary presses.

As set out above in the introductory section, (S)-[2-chloro-4-fluoro-5-(7-morpholin-4-yl-quinazolin-4-yl)phenyl]-(6-methoxy-pyridazin-3-yl)methanol has been found to exhibit valuable properties as a DNA-PK inhibitor that finds application in the treatment of cancer. It is currently being investigated in clinical trials.

Accordingly, the present invention provides the composite respectively pharmaceutical composition as described above, for use in the treatment of cancer.

Optionally the treatment of cancer further comprises radiotherapy. Suitable radiotherapy treatments are described in WO 2014/183850 and incorporated by reference herein.

Optionally, in the alternative or in addition to radiotherapy, the treatment of cancer may comprise chemotherapy. Suitable pharmaceutically active ingredients that may be used in chemotherapy in combination with (S)-[2-chloro-4-fluoro-5-(7-morpholin-4-yl-quinazolin-4-yl)phenyl]-(6-methoxy-pyridazin-3-yl)methanol include cisplatinum and etoposide or a combination thereof, to name but one example.

Accordingly, the present invention also provides a method of treating cancer in a patient in need thereof, comprising administering to the patient a pharmaceutical composition in accordance with the present invention, optionally in combination with radiotherapy or chemotherapy or both. In an exemplary embodiment, the present invention provides a method of treating a cancer selected from colon, lung, head and neck, pancreatic, and histological subtypes thereof, in a patient in need thereof, comprising administering to said patient (S)-[2-chloro-4-fluoro-5-(7-morpholin-4-yl-quinazolin-4-yl)phenyl]-(6-methoxy-pyridazin-3-yl)methanol, or a pharmaceutically acceptable salt thereof in a composite or pharmaceutical composition according to the present invention, in combination with at least one additional therapeutic agent selected from etoposide and a platin. In a further embodiment, doxorubicin may be used as a combination partner, either alone or in combination with a platin.

In the following, the present invention will be described by reference to exemplary embodiments thereof, which shall not be regarded as limiting the invention.

DETAILED DESCRIPTION OF THE INVENTION

Example 1: Preparation of crystalline anhydrous (S)-[2-chloro-4-fluoro-5-(7-morpholin-4-yl-quinazolin-4-yl)phenyl]-(6-methoxy-pyridazin-3-yl)methanol for use as a Starting Material in Hot Melt Extrusion or Melt Granulation or Spray Drying or Co-Precipitation Approx. 20 mg drug substance were dissolved or suspended in several solvents (see Table 2 below) at 50° C. The solutions/suspensions were filtered through 0.2 μm syringe filters. The obtained clear solutions were cooled down to 5° C. with a ramp of approx. 0.05 K/min. While cooling the solutions were stirred with PTFE coated stirring bars by a magnetic stirrer. The solid-/liquid-separations of obtained suspensions were done by centrifugation and the solid materials were dried overnight at room temperature with a dry nitrogen flow. The solvents used in these experiments are compiled in the table below.

| Solvent/solvent mixture | Volume [ml] |
|---|---|
| Methanol | 4 |
| Ethanol | 4 |
| 1-Propanol | 4 |
| Acetone | 4 |
| Methyl ethyl ketone | 4 |
| Methyl isobutyl ketone | 4 |
| Ethyl acetate | 4 |
| Tetrahydrofuran | 1 |
| Acetonitrile | 4 |
| H$_2$O/Dioxane, 1:1 (v:v) | 2 |
| H$_2$O Pyridine, 1:0.4 (v:v) | 1.4 |
| Methanol/Tetrahydrofuran, 1:0.4 (v:v) | 1.4 |
| Methanol/Chloroform, 1:0.2 (v:v) | 1.2 |
| Methanol/N,N-Dimethylformamide, 1:0 (v:v) | 1.3 |
| Methanol/Pyridine, 1:0.2 (v:v) | 1.2 |
| 2-Propanol/Tetrahydrofuran, 1:0.7 (v:v) | 1.7 |
| 2-Propanol/N,N-Dimethylformamide, 1:0.5 (v:v) | 1.5 |
| 2-Propanol/Pyridine, 1:0.4 (v:v) | 1.4 |
| Acetone/Dioxane, 1:0.6 (v:v) | 1.6 |
| Acetone/Tetrahydrofuran, 1:0.7 (v:v) | 1.7 |
| Acetone/Chloroform, 1:1.2 (v:v) | 2.2 |
| Acetone/N,N-Dimethylformamide, 1:0.2 (v:v) | 1.2 |
| Acetone/Pyridine, 1:0.2 (v:v) | 1.2 |

Figure 2:
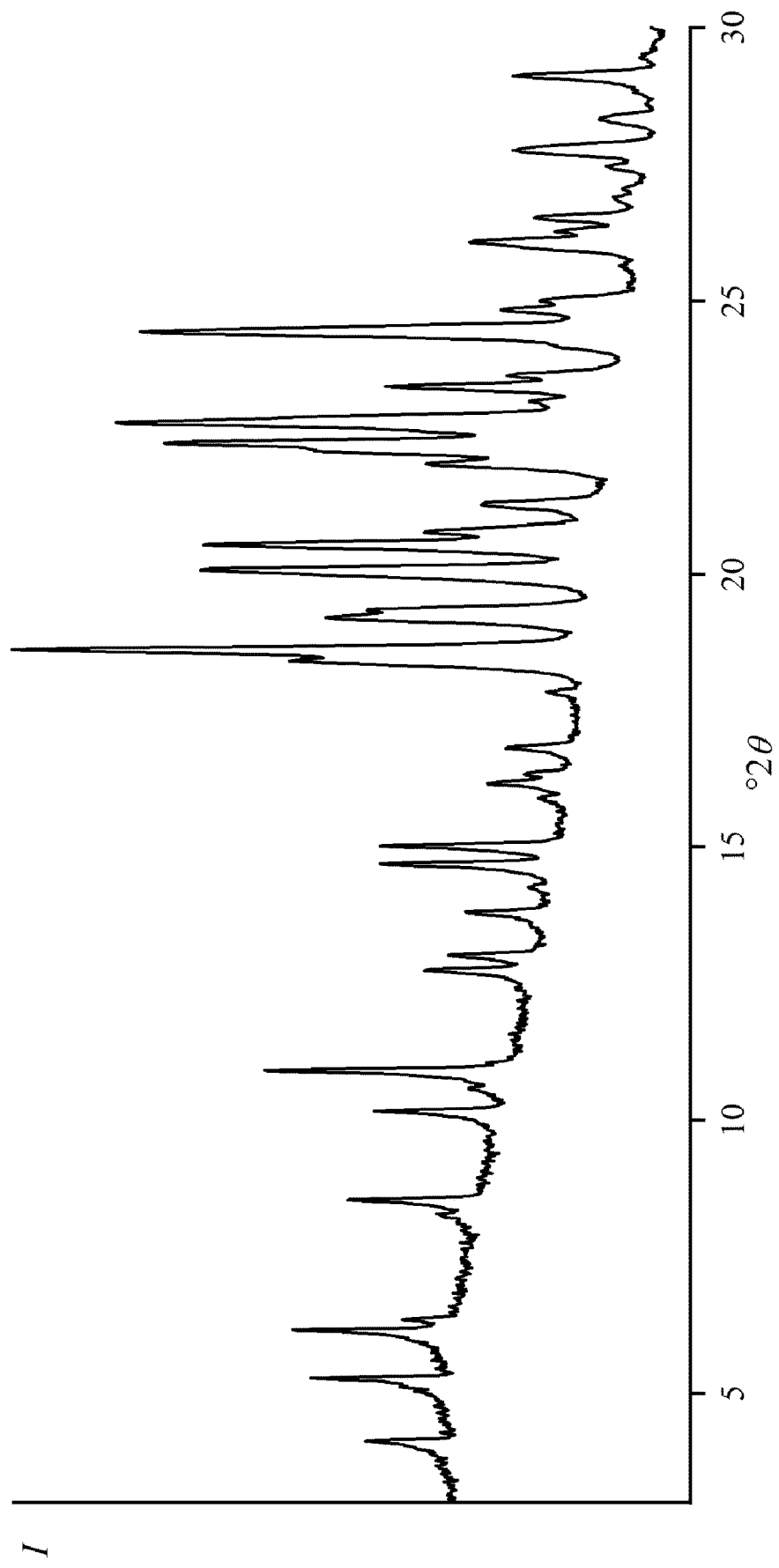
FIG. 2 shows a powder Xray diffractogram of crystalline Form I, which is preferably used as a starting material in the present invention.

X-ray powder diffraction (XRPD) was obtained by standard techniques as described in the European Pharmacopeia 7th Edition chapter 2.9.33 (Cu-K$\alpha_1$ radiation, λ=1.5406 Å, ambient temperature), and in particular: The measurement was performed in transmission geometry with Cu-K$_{\alpha 1}$ radiation on a Stoe StadiP 611 diffractometer equipped with Mythen1K Si-strip detector (PSD). Approximately 10-100 mg of the sample were prepared between amorphous films. Measurement was carried out by setting following parameters:

angular range: 1 °2θ-41 °2θ
angular resolution: 0.015 °2θ
PSD step with: 0.49 °2θ
measurement time: 15 s/PSD-step
generator settings: 40 mA, 40 kV The diffractogram is illustrated in FIG. 2 and exhibits the following peaks:

| Peak No. | °2θ (Cu—K$\alpha_1$ radiation) ± 0.2° |
|---|---|
| 1 | 4.1 |
| 2 | 5.2 |
| 3 | 6.1 |
| 4 | 8.3 |
| 5 | 8.5 |
| 6 | 10.1 |
| 7 | 10.9 |
| 8 | 12.7 |
| 9 | 13.0 |
| 10 | 13.8 |
| 11 | 14.7 |
| 12 | 15.0 |
| 13 | 18.6 |
| 14 | 19.2 |
| 15 | 20.0 |
| 16 | 20.5 |
| 17 | 20.8 |
| 18 | 21.3 |
| 19 | 22.0 |
| 20 | 22.4 |
| 21 | 22.8 |
| 22 | 23.4 |
| 23 | 24.4 |

Example 2: Solid Dispersions Prepared by Hot Melt Extrusion

Solid dispersions comprising either 20 or 30 wt. % drug substance (starting from the anhydrous crystalline Form I described above) and either 80 or 70 wt. % polymeric matrix were prepared by hot melt extrusion starting from 5 or 10 g material using a lab-scale extruder (HAAKE MiniLab II (Thermo Fisher Scientific)). The polymers used were: Aqoat®, Soluplus® and Kollidon® VA 64, which have been described in detail above, under the following conditions:

70 or 80 wt. % Kollidon® VA 64: Starting temperature extrusion: 160° C., temperature increase 5-10° C., Extrusion temperature: 200° C. (80% VA 64) or 195° C. (70% VA 64), Extrusion speed: 100 rpm (rounds per minute):

70 or 80 wt. % Aqoat®): Starting temperature extrusion: 160° C., temperature increase 5° C. (80 wt. % Aqoat®) or 5-10° C. (70 wt. % Aqoat®), Extrusion temperature: 175° C. (80% Aqoat®) or 178° C. (70% Aqoat®)), Extrusion speed: 100 rpm (rounds per minute).

70 or 80 wt. % Soluplus®: Starting temperature extrusion: 130° C. (80 wt. % Soluplus®) or 188° C. (70 wt. % Soluplus®), temperature increase 5° C. (80 wt. % Soluplus®) or 2-5° C. (70 wt. % Soluplus®), Extrusion temperature: 188° C. (80% Soluplus®) or 200° C. (70% Soluplus®), Extrusion speed: 100 rpm (rounds per minute).

Extrudates were milled using a Pulverisette 23 LabScale mill (Fritsch). At once, one strand of extrudate was milled for 2 minutes at 30 oscillations/s using two 10 mm zirconium oxide grinding ball.

Dissolution tests were run for all of the above samples, using the following test conditions: Approximately 30 mg milled extrudate were dispersed in 7 mL FaSSIF (composition see EXAMPLE 4) by shaking at 37° C. At the according time points 1 mL samples were taken, centrifuged and analysed using HPLC. Sampling time points: 5, 10, 15, 30, 60 and 120 minutes.

Figure 1:
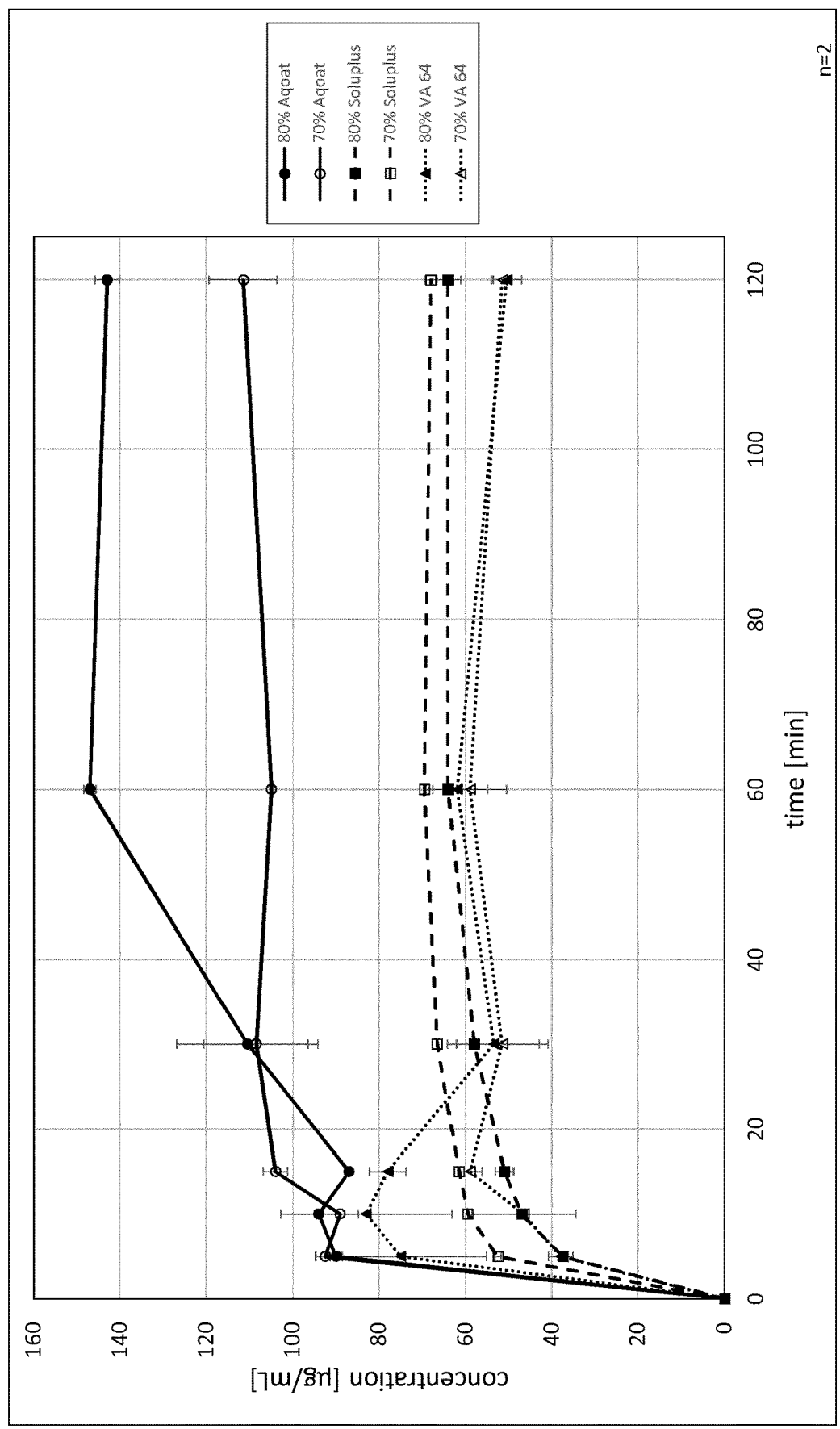
FIG. 1 shows dissolution curves for various embodiments of solid dispersions according to the present invention obtained by hot melt extrusion.

The resulting dissolution curves are illustrated in FIG. 1. As apparent from the graph, the solid dispersions of drug substance in the Aqoat® matrix provided the best dissolution for both 20 and 30 wt. % drug substance dispersions. Kollidon® VA 64 provided better dissolution at 80 wt. % polymeric matrix than the Soluplus® based formulations, but only about equivalent dissolution at 70 wt. % Kollidon® VA 64.

However, solubility of the solid dispersion is but one factor to be taken into account when assessing the quality of the solid dispersion. In terms of eutomer:distomer ratio, the Kollidon® VA 64 based solid dispersions surprisingly provided the best results, with eutomer contents of these first experimental formulations being above 95% even after 26 weeks of storage at 40° C. and 75% relative humidity. In terms of eutomer:distomer ratio, the Soluplus® based solid dispersions were clearly not as beneficial as Kollidon® VA 64 based dispersions, but still considerably better than the Aqoat® based solid dispersions.

Therefore, solid dispersions in a polymeric matrix of Kollidon® VA 64, i.e. copovidone, are particularly preferred, in particular solid dispersions of about 20 wt. % drug substance in about 80 wt. % copovidone.

X-ray diffractometric analysis of the samples revealed only amorphous material, wherein the drug substance is molecularly dispersed.

Example 3: Further Example of Solid Dispersion Prepared by Hot Melt Extrusion Further extrusion experiments were carried out on the preferred Kollidon® VA 64 (80 wt. %) based solid dispersions (i.e. 20 wt. % drug substance, starting from the anhydrous crystalline Form I described above)), using a larger scale extruder (PharmaLab 16; Thermo Fisher Scientific). The temperature profile in the extruder ranged from 60° C. at zone 2 to 150° C. at the die zone. The screw design comprised conveying elements with two kneading blocks. Screw speed was set to 300 rpm (rounds per minute) and the throughput was 1.6 kg/h. Melt temperature was estimated at about 154° C. and melt pressure at about 2 bar. The resulting solid dispersions comprised less than 0.5 wt. % of distomer. The resulting dispersion had a glass transition temperature of about 103° C. and the desired saturation solubility of more than 25 µg/mL was well reached. A hammer mill produced particles with a suitable particle size distribution, with the largest portion of the particles having a size in the range of from 100 to 355 µm.

A further extrusion experiment was carried out on the preferred Kollidon® VA 64 based solid dispersions using the larger scale extruder with an even higher drug load: 30 wt. % drug substance (as above) and 70 wt. % Kollidon® VA 64. The temperature profile in the extruder ranged from 60° C. at zone 2 to 160° C. at the die zone. The screw design comprised conveying elements with two kneading blocks. Screw speed was set to 350 rpm (rounds per minute) and the throughput was 1.0 kg/h. Melt temperature was estimated at about 160° C. and melt pressure below 1 bar. The resulting solid dispersions comprised less than 1.5 wt. % of distomer. The resulting dispersion had a glass transition temperature of about 81-83° C. A hammer mill produced particles with a suitable particle size distribution, with the largest portion of the particles having a size in the range of from 100 to 355 µm.

Thus, hot melt extrusion provided one-phasic amorphous solid dispersions, i.e. solid solutions with drugs substance molecularly dispersed in the polymeric matrix at a favourably high drug load, good bioavailability and favourably high eutomer content.

Example 4: Further Example of Solid Dispersion Prepared by Hot Melt Extrusion Further process optimization using a co-rotating twin screw extruder (ZSE 18 HP-PH; Leistritz) and a hammer mill allowed further process optimization providing even more advantageous eutomer:distomer ratios (down to 0.3 wt. % distomer), a glass transition temperature of 109° C., amorphous appearance and favourable dissolution properties in solid dispersions of 80 wt. % Kollidon® VA 64 and 20 wt. % drug substance. The results from measuring dissolution of various samples that were obtained at slightly different process conditions each (screw speed, process temperature, and feed rate) are represented in the table below:

| Sample # | Cmax90 (µg/ml) | AUC90 (min* µg/ml) | C90 (µg/ml) |
|---|---|---|---|
| 1 | 263 | 7720 | 53 |
| 2 | 257 | 8120 | 53 |
| 3 | 263 | 7460 | 51 |
| 4 | 241 | 5120 | 40 |
| 5 | 253 | 7340 | 50 |

AUC90: Area under the curve at (after) 90 minutes
C90: concentration after 90 minutes
Cmax90: maximum concentration within 90 minutes The dissolution test was carried out as follows: A 50 mg active tablet was added to a 100 mL dissolution vessel, Dissolution medium (FaSSIF pH 6.5) was prewarmed to 37° C. Paddles were run at 250 rpm. The timer was started and 100 mL dissolution medium was added to the vessel. After 1 minute, paddle speed was decreased to 200 rpm. 3 minutes before taking each sample time point, 1 mL of sample were removed with a syringe and cannula with 10 µm filter, which was then replaced with a 0.45 µm PTFE filter and the sample filtered into a HPLC vial. 50 µL filtrate were transferred into a new vial with 250 µL diluent, Samples were taken at 4, 10, 15, 20, 30, 40 and 90 minutes.

FaSSIF: 3 mM sodium taurocholate; 0.75 mM lecithin; 105.9 mM sodium chloride; 28.4 mM monobasic sodium phosphate and 8.7 mM sodium hydroxide, pH 6.5

Example 5: Exemplary Capsule Formulations

Hard gelatine capsules were provided with a filling comprising the following ingredients at the indicated weight percentage of the filling:

| Capsule # | Ingredient | wt. % |
|---|---|---|
| 1 | Solid dispersion in 80 wt % VA 64 | 50 |
|   | Sodium sulfate anhydrous | 15 |
|   | Mannitol | 15 |
|   | Crospovidone | 20 |
| 2 | Solid dispersion in 80 wt % VA 64 | 50 |
|   | Microcrystalline cellulose | 34.5 |
|   | Crospovidone | 10 |
|   | Sodium chloride | 5 |
|   | Magnesium stearate | 0.5 |
| 3 | Solid dispersion in 80 wt % VA 64 | 70 |
|   | Sodium sulfate anhydrous | 15 |
|   | Mannitol | 15 |

Example 6: Exemplary Tablet Formulations (w/o Coating)

Tablets were produced with a composition comprising the following ingredients at the indicated weight percentage of the tablet weight. A tensile strength from 1.0 to 2.0 MPa was postulated.

| Tablet # | Composition | wt. % | Disintegration time [min] |
|---|---|---|---|
| 1 | Solid dispersion in 80 % VA 64 | 50.0 | ≤15 |
|   | Microcrystalline cellulose (Avicel ® PH102) | 39.5 | |
|   | Croscarmellose sodium | 10.0 | |
|   | Magnesium stearate | 0.5 | |
| 2 | Solid dispersion in 80 wt % VA 64 | 50.0 | ≤10 |
|   | Microcrystalline cellulose (Avicel ® PH102) | 39.5 | |
|   | Crospovidone | 10.0 | |
|   | Magnesium stearate | 0.5 | |

-continued

| Tablet # | Composition | wt. % | Disintegration time [min] |
|---|---|---|---|
| 3 | Solid dispersion in 80 wt % VA 64 | 50.0 | ≤25 |
|   | Microcrystalline cellulose (Avicel ® PH102) | 44.5 | |
|   | Crospovidone | 5.0 | |
|   | Magnesium stearate | 0.5 | |
| 4 | Solid dispersion in 80 wt % VA 64 | 50.0 | ≤10 |
|   | Microcrystalline cellulose (Avicel ® PH102) | 34.5 | |
|   | Croscarmellose sodium | 10.0 | |
|   | Magnesium stearate | 0.5 | |
|   | Sodium chloride | 5.0 | |

Example 7: Therapeutic Efficacy

The therapeutic relevance of DNA-PK inhibition by the drug substance as such was investigated in vivo in combination with ionizing radiation (IR), a clinically established DSB-inducing treatment. The drug substance was tested for activity in six xenograft mouse models of human cancer. The models were chosen from different cancer indications (colon, lung, head and neck, pancreatic), and histological subtypes (adeno, squamous, large cell). Ionizing radiation was administered using a fractionated schedule of 2 Gy per day administered over five consecutive days (total radiation dose=10 Gy). was given orally 10 min prior to each fraction of radiation (ONC397-1-2AZ, ONC397-1-3AZ, ONC397-1-4AZ, ONC397-1-5AZ, ONC397-1-8AZ).

In all models, oral administration of the drug substance resulted in a strong enhancement of the radiation effect. The radiotherapy enhancing effect was quantified across the tested models by the time to reaching 400% initial volume for the 150 mg/kg study arms. The resulting Kaplan-Meier plots were compared by the log-rank test. The enhancement ratio in this treatment setting was found to be between 1.5 (A549, HCT116), and 2.6 (NCI-H460).

Example 8: Solid Dispersions Prepared by Spray Drying

Solid dispersions comprising either 10, 25 or 50 wt. % drug substance (starting from the anhydrous crystalline Form I described above) and either 50, 75 or 90 wt. % polymeric matrix were prepared by spray drying starting from 1.5 g material using a lab-scale spray dryer (4M8-TriX (ProCepT)). The polymers used were: Aqoat®, Eudragit® E PO and Kollidone VA 64, which have been described in detail above, under the following conditions:

50, 75 or 90 wt. % Aqoat®: Spray solution: 1%) (m/m) solids in 90:10 dichloromethane:methanol, inlet temperature: 80° C., air flow: 0.3 m³/min, atomizing air: 10 L/min, nozzle size: 1 mm, feed rate: 2 ml/min.

50, 75 or 90 wt. % Kollidon® VA 64: Spray solution: 2% (m/m) solids in 90:10 dichloromethane:methanol, inlet temperature: 80° C., air flow: 0.3 m³/min, atomizing air: 10 L/min, nozzle size: 1 mm, feed rate: 2 mL/min.

50, 75 or 90 wt. % Eudragit® E PO: Spray solution: 2% (m/m) solids in 90:10 dichloromethane:methanol, inlet temperature: 50° C., air flow: 0.3 m³/min, atomizing air: 10 L/min, nozzle size: 1 mm, feed rate: 2 mL/min.

Secondary drying of the spray dried material was done in a desiccator at 200 mbar. The material was fully amorphous.

Dissolution tests were run for all of the above samples, using the following test conditions: Approximately 6.5 mg solid dispersion for 10 wt. % drug substance, 2.6 mg solid dispersion for 25 wt. % drug substance and 1.3 mg solid dispersion for 50 wt. % drug substance (normalization of all tested samples to a drug substance amount of 650 µg) were weighed into a 1.5 mL Eppendorf cap.

Dissolution medium (FaSSIF pH 6.5) was prewarmed to 37° C. 1.3 mL prewarmed dissolution medium was added to the Eppendorf Cap. The sample was vortexed for 1 minute and afterwards stored at 37° C. 2.5 minutes before taking each sample time point, the sample was centrifuged for 1 minute at 10000 rpm. 50 µL supernatant were transferred into a HPLC vial with 150 µL diluent and analysed using HPLC. The remaining sample was vortexed for 25 seconds and stored at 37° C. until next time point when the procedure was repeated. Sampling time points: 5, 10, 15, 30, 60, 90 and 120 minutes.

Figure 3:
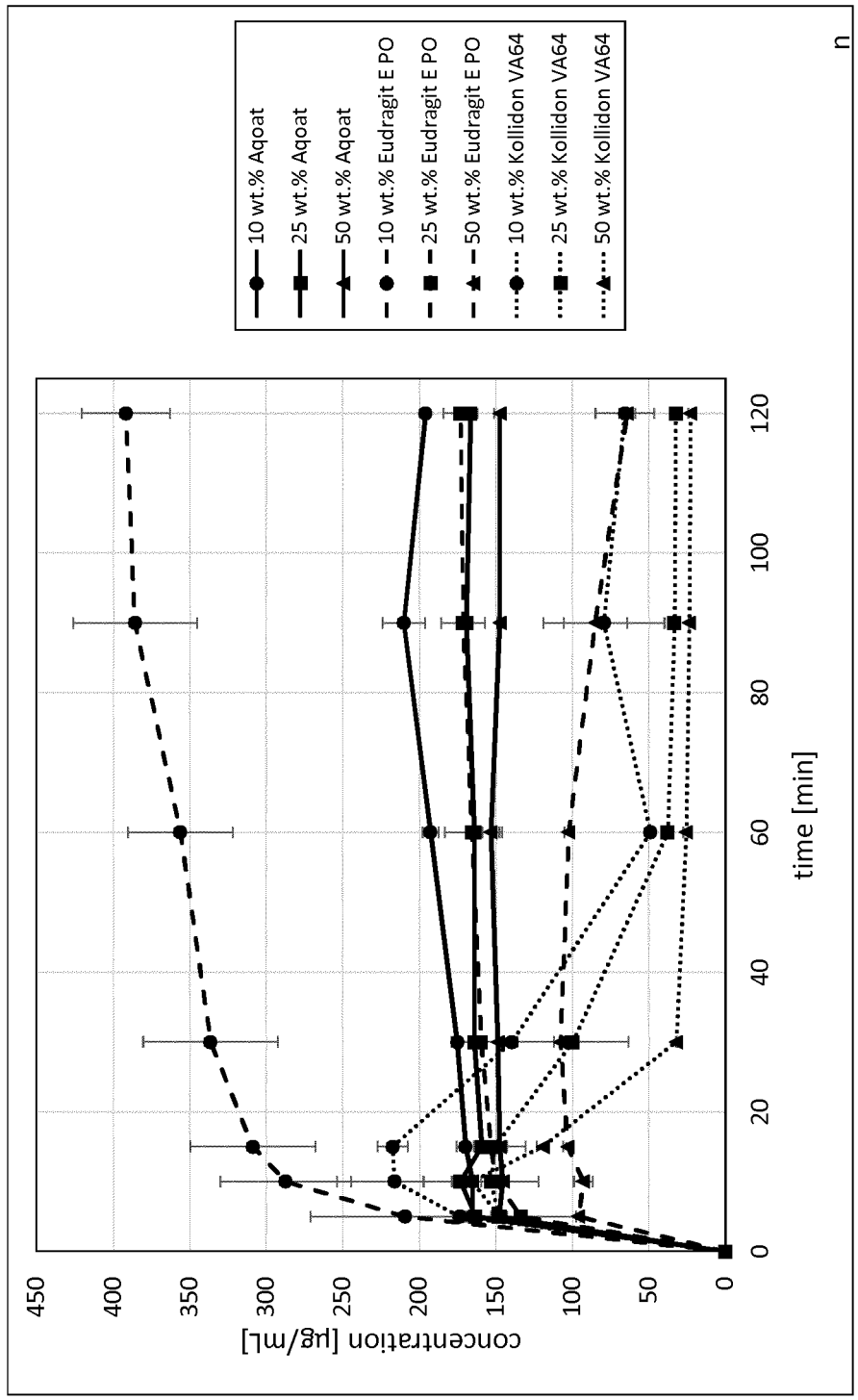
FIG. 3 shows dissolution curves for various embodiments of solid dispersions according to the present invention obtained by spray-drying.

The resulting dissolution curves are illustrated in FIG. 3.

The solid dispersion of drug substance in the Eudragit® E PO matrix provided the best dissolution for 10 wt. % drug substance dispersion. However, a clear dependence of the dissolution behaviour on the amount of drug substance within the formulation was detected.

The solid dispersion of drug substance in the Aqoat® matrix provided a clear supersaturation without precipitation. Only a slight influence of drug substance amount within the formulation was detected.

The solid dispersion of drug substance in the Kollidon® VA64 matrix provided a clear supersaturation with subsequent precipitation. Only slight influence of drug substance amount within the formulation was detected. The 10 wt. % drug substance dispersion showed the highest supersaturation whereas the 25 wt. % and 50 wt. % drug substance dispersions showed almost the same supersaturation and precipitation.

However, solubility of the solid dispersion is but one factor to be taken into account when assessing the quality of the solid dispersion. In terms of stability:

The solid dispersion of drug substance in the Aqoat® matrix showed only negligible loss in dissolution performance. After 12 weeks of storage at 40° C. and 75% relative humidity X-ray diffractometric analysis of the samples revealed only amorphous material. Only an acceptable increase in impurities was detected, The solid dispersion of drug substance in the Kollidon® VA64 matrix showed no change in dissolution performance over time. After 12 weeks of storage at 25° C. and 60% relative humidity X-ray diffractometric analysis of the samples revealed only amorphous material, Only a very small increase in impurities was detected (even less than in the Aqoat matrix).

While the solid dispersions of drug substance in the Eudragit® E PO matrix showed the best dissolution, dissolution performance and impurity levels after 12 weeks of storage at 40° C. and 75% relative humidity were notably inferior as compared to the Kollidon® VA64 and Aqoat® matrix dispersions.

Therefore, solid dispersions in a polymeric matrix of HPMCAS, herein Aqoat®, manufactured by spray drying are amongst the particularly preferred embodiments, in particular solid dispersions of about 25 wt. % drug substance in about 75 wt. % HPMCAS.

Example 9: Further Examples of Solid Dispersions Prepared by Spray Drying

Further spray drying experiments were carried out on Aqoat® (75 wt. %) based solid dispersions, using a custom-built lab-scale spray dryer. Spray drying was performed under the following conditions:

Spray solution: 6 wt. % solids in 90:10 dichloromethane:methanol, temperature: 96° C., gas flow rate: 450 g/min, atomizing pressure: 120 psi, atomizer: pressure Swirl Schlick 2.0, Feed rate: 27 g/min.

Secondary drying of the spray dried material was done in a convection tray dryer at 40° C. for 22 hours.

X-ray diffractometric analysis of the sample revealed only amorphous material,

In terms of eutomer:distomer ratio, the obtained Aqoat® based solid dispersion provided eutomer contents above 95%, even after 26 weeks of storage at 40° C. and 75% relative humidity. Advantageously, the sum of total degradation products was smaller than 2%.

Example 10: Solid Dispersions Prepared by Coprecipitation

Solid dispersions comprising either 20 or 35 wt. % drug substance (using the anhydrous crystalline Form I described above in the preparation) and either 80 or 65 wt. % polymeric matrix were prepared by coprecipitation screening. The polymers used were: HPMCAS and HPMCP, which have been described in detail above.

A clear solution of compound and polymer (about 20 or 35 wt. % of compound to polymer) in DMA is prepared. 70 μL of the clear DMA solution is poured drop-wise by a multi-channel pipette to a chilled and vigorously stirred antisolvent (700 μL HCl solution, 0.01N, pH 2) in 1-mL glass vials. The resulting suspension is filtered and the obtained cake is washed with water and dried under vacuum.

X-ray diffractometric analysis of the solid dispersions showed no evidence of crystalline material for both drug substance concentrations in HMPCAS and HPMCP.

Example 11: Analytical Methods

The solid state, and in particular amorphous nature of the resulting solid dispersions can be assessed by X-ray diffractometric measurements and/or by DSC measurements, with suitable methods employed for analysis of the preceding examples described in the following. It will be apparent to the skilled person that for certain embodiments, modifications of the analytical methods may be necessary or advantageous. Such modifications, such as adaptation of the heating ramp rate, will be readily identifiable by the skilled person.

XRD:

Measurements were performed in transmission geometry with Cu-K$\alpha_1$ radiation on a Stoe StadiP 611 diffractometer equipped with Mythen1K Si-strip detector (PSD) by setting following parameters:
preparation between amorphous films
angular range: 1 °2θ-41 °2θ
angular resolution: 0.03 °2θ
PSD stepwith: 0.09 °2θ
measurement time: 60 s/PSD-step
generator settings: 40 mA, 40 kV

DSC:

DSC studies were performed on a DSC 1 (Mettler Toledo, Switzerland). 20 mg solid dispersion, for instance milled extrudate, were weighed into a 100 μL DSC aluminum crucible and sealed with a lid, which was punctured manually before the measurement. Three heating cycles were carried out: from 25 to 180° C. at a ramp rate of 5 K/min, then maintain at 180° C. for 5 minutes, and then cool down from 180° C. to 25° C. at −5 K/min. During the fourth heating cycle, heating from 25 to 180° C. was effected at a ramp rate of only 10 K/min. Glass transition temperatures Tg were determined in the second, third and fourth heating cycles.

A single glass transition temperature is indicative of an one-phase amorphous system.

HPLC:

Integrity of the drug substance, in particular with regard to possible degradation products, can be assessed by HPLC as follows:

System: Agilent Technologies (USA) 1260 HPLC System
Method: 10 μL of sample were injected and quantified by a diode array detector working at 298 nm. The eluents used were binary mixtures of 95:5 and 5:95 (v/v) MilliQ water with 0.1% trifluoric acid and ACN. The linear gradient ran from 90% phase A to 100% B within 13 min. A YMC Triart reverse phase column (4.6×50 mm with 3 μm packing) was used, constantly heated up to 35° C.

The degree of enantiomeric impurity can be assessed using quantitative chiral HPLC as follows:

System: Agilent Technologies (USA) 1260 HPLC System
Method: 5 μL of sample were injected and quantified by a diode array detector working at 273 nm. The eluents used were n-Hexane with 0.1% formic acid (phase A) and Isopropanol with 0.1% formic acid (phase B). The isocratic gradient with 80% phase A and 20% phase B ran within 40 min. A Lux Cellulose-1 column (4.6×150 mm with 5 μm packing) was used, constantly heated up to 20° C.

The invention claimed is:

1. A composite, comprising:
   a solid dispersion of (S)-[2-chloro-4-fluoro-5-(7-morpholin-4-yl-quinazolin-4-yl)phenyl]-(6-methoxy-pyridazin-3-yl)methanol, or a pharmaceutically acceptable salt thereof,
   in a polymeric matrix consisting of a copolymer of polyvinylpyrrolidone and polyvinyl acetate.

2. The composite according to claim 1, consisting of:
   the solid dispersion of (S)-[2-chloro-4-fluoro-5-(7-morpholin-4-yl-quinazolin-4-yl)phenyl]-(6-methoxy-pyridazin-3-yl)methanol, or the pharmaceutically acceptable salt thereof,
   in the polymeric matrix.

3. The composite according to claim 1, wherein (S)-[2-chloro-4-fluoro-5-(7-morpholin-4-yl-quinazolin-4-yl)phenyl]-(6-methoxy-pyridazin-3-yl)methanol is present in its free form.

4. The composite according to claim 1, wherein the solid dispersion is a solid solution.

5. The composite according to claim 1, wherein the solid dispersion is obtainable by hot melt extrusion.

6. The composite according to claim 1, wherein a concentration of (S)-[2-chloro-4-fluoro-5-(7-morpholin-4-yl-quinazolin-4-yl)phenyl]-(6-methoxy-pyridazin-3-yl)methanol, which may be present in free form or as a pharmaceutically acceptable salt, in the polymeric matrix is in a range of between 4 and 50 weight percent, based upon the total weight of the solid dispersion.

7. The composite according to claim 1, wherein the composite has a particle size characterized by a d50 value of 1000 μm or less.

8. A pharmaceutical composition, comprising:
   the composite according to claim 1.

9. The pharmaceutical composition according to claim 8, which is for oral administration.

10. The pharmaceutical composition according to claim 8, which is an immediate release composition.

11. The pharmaceutical composition according to claim 8, characterized by a disintegration time of 15 minutes or less.

12. The pharmaceutical composition according to claim 8, which is a capsule containing a filling, wherein the filling comprises the composite and optionally at least one pharmaceutically acceptable excipient.

13. The pharmaceutical composition according to claim 12, which is a capsule, which contains the filling consisting of:
    40 to 100 wt. % of the composite; and
    0 to 60 wt. % of the at least one pharmaceutically acceptable excipient, based upon the total weight of the filling.

14. The pharmaceutical composition according to claim 8, wherein the pharmaceutical composition comprises at least one pharmaceutically acceptable excipient, and wherein the pharmaceutical composition is selected from the group consisting of a tablet and a granulate.

15. The pharmaceutical composition according to claim 14, which is a tablet,
    wherein the at least one pharmaceutically acceptable excipient is selected from the group consisting of a filler, a disintegrant, a lubricant, a pore builder, and an inorganic alkaline metal salt.

16. The pharmaceutical composition according to claim 14, which is a tablet, comprising:
    25 to 95 wt. % of the composite;
    15 to 72.5 wt. % of a filler;
    2.5 to 40 wt. % of a disintegrant;
    0 to 5 wt. % of a lubricant;
    0 to 20 wt. % of an inorganic alkaline metal salt; and
    a total of 0 to 20 wt. % of one or more additional pharmaceutically acceptable excipients,
    based upon the total weight of the tablet.

17. The pharmaceutical composition according to claim 14, which is a tablet, comprising:
    40 to 60 wt. % of the composite;
    25 to 55 wt. % of a filler;
    5 to 30 wt. % of a disintegrant;
    0 to 5 wt. % of a lubricant;
    0 to 15 wt. % of an inorganic alkaline metal salt; and
    a total of 0 to 10 wt. % of one or more additional pharmaceutically acceptable excipients,
    based upon the total weight of the tablet.

18. The pharmaceutical composition according to claim 14, which is a tablet, comprising:
    35 to 55 wt. % of the composite;
    30 to 55 wt. % of a filler;
    5 to 20 wt. % of a disintegrant;
    0.25 to 2.5 wt. % of a lubricant;
    2.5 to 15 wt. % of an inorganic alkaline metal salt; and
    a total of 0 to 10 wt. % of one or more additional pharmaceutically acceptable excipients,
    based upon the total weight of the tablet.

19. The pharmaceutical composition according to claim 14, wherein the at least one pharmaceutically acceptable excipient is selected from the group consisting of a filler, a disintegrant, an inorganic alkaline metal salt, and a combination thereof, and wherein
    the filler is microcrystalline cellulose,
    the disintegrant is selected from the group consisting of crospovidone, carboxymethylcellulose, and salts or derivatives thereof, and
    the inorganic alkaline metal salt is an inorganic sodium salt.

20. A method of treating cancer in a patient in need thereof, comprising:
    administering to the patient the pharmaceutical composition according to claim 8, optionally in combination with radiotherapy or chemotherapy or both.

21. The method of treating cancer according to claim 20, wherein said method further comprises:
    administering at least one chemotherapy drug selected from the group consisting of cisplatin, etoposide and doxorubicin.

22. A method for preparing the composite according to claim 1, the method comprising:
    hot melt extruding or melt granulating to form the composite.

23. A method for preparing the composite according to claim 1, the method comprising:
    mixing and melting (S)-[2-chloro-4-fluoro-5-(7-morpholin-4-yl-quinazolin-4-yl)phenyl]-(6-methoxy-pyridazin-3-yl)methanol or a pharmaceutically acceptable salt thereof and the copolymer of polyvinylpyrrolidone and polyvinyl acetate, and optionally at least one pharmaceutically acceptable excipient,
    hot melt extruding or melt granulating the mixture to form the composite, and
    optionally milling the formed composite.

24. A method for preparing the composite according to claim 1, the method comprising:
    dissolving (S)-[2-chloro-4-fluoro-5-(7-morpholin-4-yl-quinazolin-4-yl)phenyl]-(6-methoxy-pyridazin-3-yl)methanol or a pharmaceutically acceptable salt thereof and the copolymer of polyvinylpyrrolidone and polyvinyl acetate, and optionally one or more pharmaceutically acceptable excipients, in a solvent to form a solution,
    spray-drying the solution to form the composite, and
    optionally drying the composite.

25. A method for preparing a pharmaceutical composition, comprising the composite according to claim 1, the method comprising:
    preparing the composite by
        mixing and melting (S)-[2-chloro-4-fluoro-5-(7-morpholin-4-yl-quinazolin-4-yl)phenyl]-(6-methoxy-pyridazin-3-yl)methanol or a pharmaceutically acceptable salt thereof and the copolymer of polyvinylpyrrolidone and polyvinyl acetate;
        hot melt extruding or melt granulating the mixture to form the composite, and
        optionally milling the formed composite; or
        dissolving the (S)-[2-chloro-4-fluoro-5-(7-morpholin-4-yl-quinazolin-4-yl)phenyl]-(6-methoxy-pyridazin-3-yl)methanol or the pharmaceutically acceptable salt thereof and polyvinylpyrrolidone and polyvinyl acetate in a solvent to form a solution,
        spray-drying the solution to form the composite, and
        optionally drying the composite,
    mixing the composite and one or more pharmaceutically acceptable excipients;
    optionally granulating the mixture of the composite and the one or more pharmaceutically acceptable excipients, and
    either filling the mixture into capsules or tableting the mixture.

26. The composite according to claim 1, wherein the solid dispersion is obtainable by melt granulation.

27. The composite according to claim 1, wherein the solid dispersion is obtainable by spray drying.

\* \* \* \* \*

UNITED STATES PATENT AND TRADEMARK OFFICE
CERTIFICATE OF CORRECTION

PATENT NO. : 11,559,490 B2
APPLICATION NO. : 16/498943
DATED : January 24, 2023
INVENTOR(S) : Geissler et al.

It is certified that error appears in the above-identified patent and that said Letters Patent is hereby corrected as shown below:

On the Title Page

Item (56), Column 2, Line 12, in OTHER PUBLICATIONS currently reads:
"Lekarstvenneye"
And should read:
--Lekarstvennye--;

Item (56), Column 2, Line 13, in OTHER PUBLICATIONS currently reads:
"Ed.,Moscow:"
And should read:
--Ed., Moscow:--;

Item (56), Column 2, Lines 21-22, in OTHER PUBLICATIONS currently reads:
"TPU, 2003, pp. 2 and 142. Flynn et al., "Pharmacokinetic Parameters", New Jersey Medical school, 2007, pp. 1-3."
And should read:
--TPU, 2003, pp. 2 and 142.
Flynn et al., "Pharmacokinetic Parameters", New Jersey Medical school, 2007, pp. 1-3.--.

Signed and Sealed this
Eighteenth Day of July, 2023

Katherine Kelly Vidal
*Director of the United States Patent and Trademark Office*